United States Patent [19]

Mar

[11] Patent Number: 4,771,778
[45] Date of Patent: Sep. 20, 1988

[54] STEERABLE LOW PROFILE BALLOON DILATATION CATHETER

[75] Inventor: Craig E. Mar, Fremont, Calif.

[73] Assignee: Advanced Cardiovascular Systems, Inc., Mountain View, Calif.

[21] Appl. No.: 650

[22] Filed: Jan. 6, 1987

[51] Int. Cl.$^4$ ............................................. A61M 29/02
[52] U.S. Cl. ........................................ 128/344; 604/96
[58] Field of Search ............... 128/344, 348.1; 604/96, 604/164, 166, 170, 97, 98

[56] References Cited

U.S. PATENT DOCUMENTS

| | | | |
|---|---|---|---|
| 3,906,938 | 9/1975 | Fleischhacker | 604/170 |
| 4,261,339 | 4/1981 | Hanson et al. | 128/344 |
| 4,483,340 | 11/1984 | Fogarty et al. | 128/344 |
| 4,538,622 | 9/1985 | Samson et al. | 604/170 |
| 4,545,390 | 10/1985 | Leary | 128/344 |
| 4,554,929 | 11/1985 | Samson et al. | 604/164 |
| 4,638,805 | 1/1987 | Powell | 128/344 |

FOREIGN PATENT DOCUMENTS 0213748 3/1987 European Pat. Off. ............ 628/344

*Primary Examiner*—C. Fred Rosenbaum
*Assistant Examiner*—Gene B. Kartchner
*Attorney, Agent, or Firm*—Fulwider, Patton, Rieber, Lee & Utecht

[57] ABSTRACT

Steerable low profile dilatation catheter having a flexible elongate tubular member with proximal and distal extremities and with a flow passage extending therethrough. An adapter is secured to the proximal extremity of the tubular member. A separate balloon having proximal and distal extremities is provided. The balloon has its proximal extremity mounted on the distal extremity of the flexible elongate tubular member. A core wire extends through the flow passage of the tubular member and through the balloon and beyond the distal extremity of the balloon. A tip coil is provided which is formed of a radiopaque material and has proximal and distal extremities. The proximal extremity of the tip coil is secured to the distal extremity of the balloon. The distal extremity of the core wire extends into the tip coil but is spaced from the distal extremity of the tip coil.

7 Claims, 1 Drawing Sheet

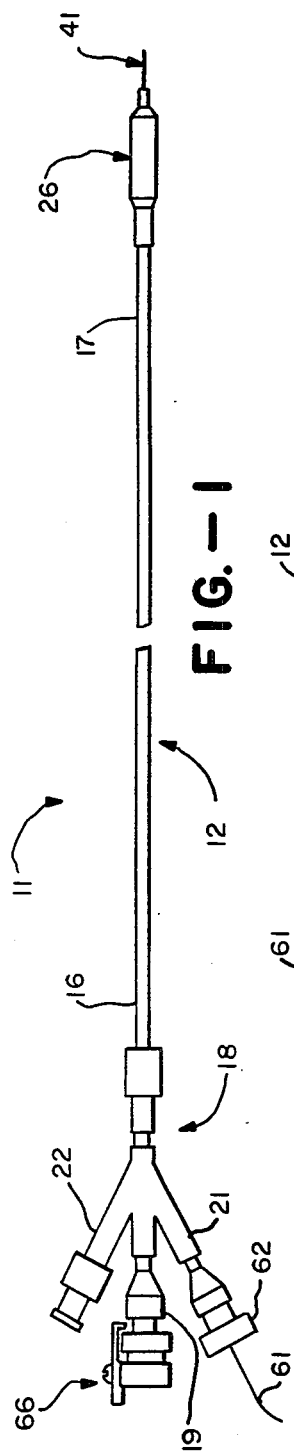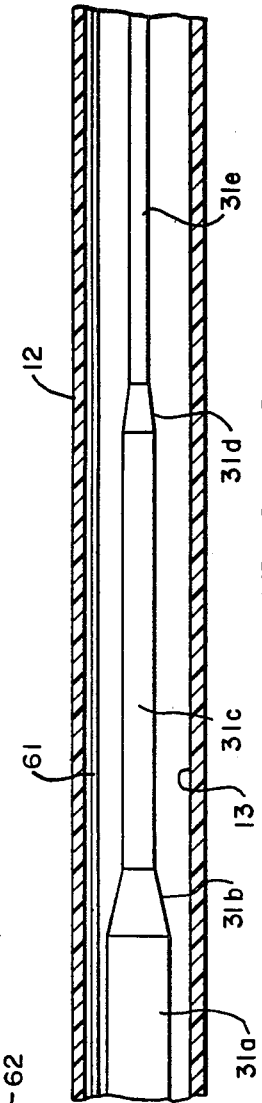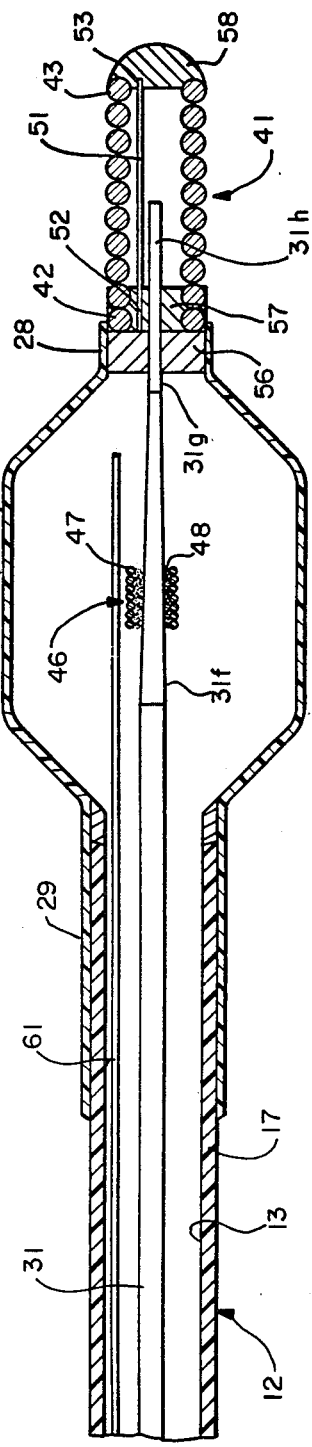

STEERABLE LOW PROFILE BALLOON DILATATION CATHETER

This invention relates to a steerable low profile balloon dilatation catheter, and more in particular, to a dilatation catheter of this type in which the balloon is formed on the core wire.

Low profile balloon dilatation catheters have heretofore been provided of a steerable type such as that disclosed in U. S. Pat. No. 4,582,181. However, there is still a need for such steerable dilatation catheters having smaller balloon profiles.

In general, it is an object of the present invention to provide a steerable low profile balloon dilatation catheter having a small low profile balloon.

Additional objects and features of the invention will appear from the following description in which the preferred embodiment is set forth in detail in conjunction with the accompanying drawing.

FIG. 1 is a plan view of a steerable low profile balloon dilatation catheter incorporating the present invention.

FIG. 2 is an enlarged cross-sectional view of a portion of the catheter shown in FIG. 1 just proximal of the balloon.

FIG. 3 is an enlarged cross sectional view of the distal extremity of the catheter shown in FIG. 1.

In general, the steerable low profile balloon dilatation catheter is comprised of a flexible elongate tubular member having proximal and distal extremities and having a flow passage extending therethrough. An adapted is secured to the proximal extremity of the tubular member. A separate balloon member having proximal and distal extremities is provided. The proximal extremity of the balloon member is mounted on the distal extremity of the flexible elongate tubular member to form a liquid-tight seal between the same. A core wire extends through the flow passage of the tubular member and through the balloon and beyond the distal extremity of the balloon. A tip coil formed of a radiopaque material having proximal and distal extremities is provided. Means is provided for securing the proximal extremity of the tip coil in the distal extremity of the balloon member. The distal extremity of the core wire extends into the tip coil but is spaced from the distal extremity of the tip coil. A shaping ribbon having proximal and distal extremities is provided. Means is provided for securing the proximal extremity of the shaping ribbon to the distal extremity of the core wire. Means is also provided for securing the distal extremity of the shaping ribbon to the distal extremity of the tip coil.

More in particular as shown in the drawings, the steerable low profile balloon dilatation catheter 11 consists of a flexible elongate tubular member 12 which is provided with a flow passage or lumen 13 extending therethrough. The tubular member 12 provides the shaft tubing for the dilatation catheter 11 and can be formed of a suitable material such as polyethylene and can have suitable dimensions, as for example 0.040 inches outside diameter and an inside diameter of 0.030 inches to provide a wall thickness of 0.005 inches. A low density polyethylene can be utilized for the tubular member 12. However, if additional stiffness is desired in the tubular member, particularly at the proximal extremity thereof, a polyethylene of high density can be utilized or mixed with the low density polyethylene.

The tubular member 12 is provided with proximal and distal extremities 16 and 17. An adapter 18 of a conventional type is mounted on the proximal extremity of the tubular member and is provided with a central arm 19 and side arms 21 and 22 which are utilized for purposes hereinafter described. All of the arms 19, 21 and 22 are in communication with the lumen or flow passage 13.

A balloon member 26 is provided and can be formed of a suitable material such as an irradiated polyethylene having a relatively thin wall thickness, as for example, a wall thickness of 0.001 inch. The balloon member 26 provides a balloon 27 of a suitable outside diameter when inflated of approximately 1.5 to 2.5 millimeters. The balloon 27 when deflated can have a profile of approximately 0.025 inch. The distal extremity 28 of the balloon member 26 is also of a suitable diameter such as 0.025 inch. The proximal extremity 29 of the balloon member 26 is mounted on the distal extremity 17 of the tubular member 12, It is secured thereto in a manner to form a liquid-tight seal between the balloon member 26 and the distal extremity of the tubular member 12. By way of example, the proximal extremity 28 can be heat shrunk onto the distal extremity 17 of the tubular member 12. If desired suitable means such as an adhesive can be utilized for making this connection. With the balloon member 26 mounted on the distal extremity 17 of the tubular member, the tubular member has an outside diameter of approximately 0.042 inch.

A core wire 31 (see FIG. 2) is provided to facilitate steering of the dilatation catheter. The core wire 31 is provided with a distal extremity 33. The core wire 31 can be formed of a suitable material such as stainless steel. The core wire 31 can have suitable dimensions, as for example, the proximal portion 31a of the core wire 31 and the portion of the core wire 31 extending through substantially the entire tubular member 12 can have a continuous cylindrical diameter of approximately 0.016 inch. Commencing within a region proximal to the balloon 26, the core wire 31 can be provided with a tapered portion 31b in which the diameter of the core wire 31 is reduced from 0.016 inch to approximately 0.008 inch. The tapered portion 31b is followed by a portion 31c ten centimeters in length of a continuous diameter of 0.008 inch. This is followed by a tapered portion 31d having a length of 3 centimeters reducing the diameter from 0.008 inch to 0.003 inch. The core wire is then provided with a portion 31e having a continuous diameter of 0.005 inch. A tapered portion 31f follows in which the diameter is reduced from 0.005 inch to 0.003 inch. Portion 31f is followed by a portion of continuous diameter 31g of 0.003 inch. The distal portion 31g is flattened to provide a distal extremity which has a width of approximately 0.004 inches and a thickness of approximately 0.002 inches. The flattened distal portion 31h can have a suitable length, as for example, one half to one centimeter.

A tip coil 41 of a suitable length of one to 3 centimeters is provided which is formed of a suitable radiopaque material such as platinum wire having a suitable diameter such as 0.003 inches wound on a mandrel of a suitable diameter such as 0.010 inches. The tip coil 41 is provided with proximal and distal extremities 42 and 43. A marker 46 is provided which is formed of a suitable material such as a coil 47 of platinum wire which is secured to the core wire 31 within the balloon 27 equidistant the ends of the balloon by suitable means such as an adhesive 48.

A shaping ribbon 51 is provided which can be formed of a suitable material such as stainless steel. The shaping ribbon can be of any desired cross section, as for example, it can be rectangular having a thickness of 0.001 inches and a width of 0.003 inches. The shaping ribbon 51 is provided with proximal and distal extremities 52 and 53 and has a length so that the distal extremity can be substantially co-extensive with the distal extremity of the tip coil 41 and its proximal extremity 52 be substantially co-extensive with the proximal extremity of the tip coil 41.

From FIG. 3, it can be seen that the distal extremity of the core wire 31 and in particular the flattened end portion 31h extends beyond the distal extremity 28 of the balloon member 26 and approximately half-way into the tip coil 41 and terminates short of the distal extremity of the tip coil 41. Means is provided for forming a liquid-tight seal between the distal extremity 29 of the balloon member 26 and the portion 31g of the core wire 31 such as an adhesive 56. Means is also provided for securing the proximal extremity 42 of the tip coil 41 and the proximal extremity 52 of the shaping ribbon 51 to the portion 31g of the core wire 31 by suitable means such as solder 57. Means is also provided for securing the distal extremity 53 of the shaping ribbon 51 to the distal extremity of the tip coil 41 and consists of solder to provide a rounded hemispherical tip 58. A vent tube 61 is provided which extends through a fitting 62 provided on the side arm 21 which can form a liquid-tight seal with the same. The vent tube 61 extends into the distal region of the balloon 27 and is utilized for venting air from the interior of the balloon when the balloon is filled with a suitable fluid, as for example, a radiopaque contrast liquid through the side arm 22 by the use of suitable inflation/deflation means such as described in U.S. Pat. No. 4,439,185.

Means is provided for rotating the proximal extremity 32 of the core wire 31 and consists of a rotation limiting device 66 which is mounted on the central arm 19. This rotation limiting device can be of the type described in U.S. Pat. No. 4,619,263.

Operation and use of the steerable balloon dilatation catheter 11 may now be briefly described as follows. Let it be assumed that it is desired to utilize the dilatation catheter in an angioplasty procedure. Prior to insertion of the dilatation catheter 11 into the vessel of the patient, the balloon 27 is inflated by applying an inflation/deflation device to the side arm 22 to introduce the radiopaque contrast liquid into the flow passage 13 into the interior of the balloon. Any air within the balloon is exhausted to the atmosphere through the vent tube 61. There is adequate room for the flow of the liquid between the 0.016 inch core wire and the 0.030 inch inside diameter of the tubular member 12. After the balloon has been inflated, the vent tube 61 can be removed. The balloon can then be deflated so that it is ready for use.

After the guiding catheter has been positioned in the patient vessel, the balloon dilatation catheter of the present invention can be utilized. A prebend, if such is desired, can be provided in the tip coil 41 which can be formed to retain a desired shape because of the safety ribbon 51 provided therein. The dilatation catheter can then be inserted into the guiding catheter in the patient vessel and advanced into a region near the stenosis. If it is desired to rotate the dilatation catheter and particularly the tip of the same to advance into a particular tight stenosis or one which is at an angle, the rotation limiting device 66 can be rotated to cause rotation of the distal extremity of the tip coil. Movement of the tip coil can be observed under the fluoroscope because of its radiopacity. The coil tip 41 is then advanced into the stenosis. The balloon 27 can readily follow because of its reduced profile. The positioning of the balloon 27 can be observed by observing the location of the marker 46. After the balloon has been positioned in the stenosis, the balloon can be inflated by again introducing a radiopaque contrast liquid through the side arm 22 through the flow passage 13 into the interior of the balloon 27. After the balloon 27 has been inflated for a predetermined period of time, the balloon can be deflated and the dilatation catheter withdrawn from the stenosis and the guiding catheter.

If it is desired to create a still larger opening in the stenosis, a larger balloon can then be introduced into the guiding catheter and advanced in the stenosis with the balloon being inflated to further increase the size in the stenosis. This second balloon dilatation catheter can then be removed after which the guiding catheter can be removed to complete the angioplasty procedure.

I claim:

1. A steerable low profile dilatation catheter comprising a flexible elongate tubular member having proximal and distal extremities and having a flow passage extending therethrough, an adapted secured to the proximal extremity of the tubular member, a separate, relatively thin-walled balloon member having proximal and distal extremities and having its proximal extremity mounted on the distal extremity of the flexible elongate tubular member to provide a liquid-tight seal between the same, a core wire extending through the flow passage of the tubular member and through the balloon with the distal extremity thereof extending beyond the distal extremity of the balloon, a tip coil formed of a radiopaque material having proximal and distal extremities, means to provide a liquid-tight seal between the distal extremity of the balloon and the core wire extending therethrough, means securing the proximal extremity of the tip coil to the core wire extending out of the distal end of the balloon, the distal extremity of the tip coil being spaced from the distal extremity of the core wire and a shaping member secured at the distal extremity thereof to the distal extremity of the tip coil and the proximal extremity thereof to the core wire.

2. A dilatation catheter as in claim 1 wherein said core wire is provided with a tapered distal extremity.

3. A dilatation catheter as in claim 2 wherein said core wire is provided with a proximal portion having a continuous diameter of approximately 0.016 inch for a substantial portion of the same and wherein the portion of the guide wire extending into the balloon has a tapered portion reducing the diameter from approximately 0.016 inch to approximately 0.008 inch, a taper portion reducing the diameter from approximately 0.008 inch to approximately 0.005 inch.

4. A dilatation catheter as in claim 1 wherein the the shaping member is provided with a flattened distal end portion.

5. A dilatation catheter as in claim 4 wherein the flattened end portion exceeds into the tip coil.

6. A dilatation catheter as in claim 1 wherein the balloon member has a wall thickness which is substantially less than the wall thickness of the tubular member.

7. A dilatation catheter as in claim 1 wherein said tubular member has a wall thickness of approximately 0.005 inch and the balloon member has a wall thickness of approximately 0.001 inch.

* * * * *

UNITED STATES PATENT AND TRADEMARK OFFICE
CERTIFICATE OF CORRECTION

PATENT NO. : 4,771,778

DATED : September 20, 1988

INVENTOR(S) : Craig E. Mar

It is certified that error appears in the above-identified patent and that said Letters Patent is hereby corrected as shown below:

Column 1, line 33, delete "adapted" and insert therefor --adapter--.

Column 2, line 19, after "12" delete "," and insert therefor --.--.

Column 4, line 25, delete "adapted" and insert therefor --adapter--.

Column 4, line 60, delete "exceeds" and insert therefor --extends--.

Signed and Sealed this

Twenty-fourth Day of October, 1989

Attest:

DONALD J. QUIGG

Attesting Officer

Commissioner of Patents and Trademarks